United States Patent
Omura et al.

(10) Patent No.: US 6,280,749 B1
(45) Date of Patent: Aug. 28, 2001

(54) PARTICLES OF CURED FLUOROSILICONE RUBBER AND COSMETIC PREPARATION CONTAINING SAME

(75) Inventors: Naoki Omura; Yoshinori Inokuchi; Satoshi Kuwata, all of Gunma-ken (JP)

(73) Assignee: Shin-Etsu Chemical Co., Ltd. (JP)

( * ) Notice: Subject to any disclaimer, the term of this patent is extended or adjusted under 35 U.S.C. 154(b) by 0 days.

(21) Appl. No.: 09/351,905

(22) Filed: Jul. 14, 1999

(30) Foreign Application Priority Data

Jul. 15, 1998 (JP) .................................................. 10-200779

(51) Int. Cl.$^7$ ............................ A61K 7/00; A61K 7/032; A61K 31/695; A61K 31/775
(52) U.S. Cl. ........................... 424/401; 424/489; 424/63; 424/69; 423/324; 423/348; 524/588
(58) Field of Search ...................... 424/401, 489, 424/63, 69, 78.03, 78.08; 524/588; 106/287.13; 525/477; 528/42; 423/348, 324

(56) References Cited

U.S. PATENT DOCUMENTS

| 4,594,134 | 6/1986 | Hanada et al. | |
|---|---|---|---|
| 4,983,388 | * 1/1991 | Kuwata et al. | 424/401 |
| 5,342,879 | * 8/1994 | Takahashi et al. | 524/588 |
| 5,871,761 | * 2/1999 | Kuwata et al. | 424/401 |

FOREIGN PATENT DOCUMENTS

| 551211 | 7/1993 | (EP) . |
|---|---|---|
| 4159370 | 6/1992 | (JP) . |
| 08310915 | 11/1996 | (JP) . |

OTHER PUBLICATIONS

EP Search Report dated Oct. 25, 1999.
Patent Abstracts of Japan, vol. 97, No. 3, Mar. 31, 1997 & JP 08 310915 A (Shiseido), abstract.
Database WPI, Week 9229, Derwent Publications Ltd., London, GB; AN 1992–238165 & JP 04 159370 A (Toshiba Silicone), abstract 1992.

* cited by examiner

Primary Examiner—Diana Dudash
Assistant Examiner—Mina Haghighatian
(74) Attorney, Agent, or Firm—Millen, White, Zelano & Branigan, P.C.

(57) ABSTRACT

Disclosed is a powder consisting of particles of a cured fluoro-silicone rubber having a specified average particle diameter and a specified rubber hardness. The fluorosilicone rubber has a siloxane composition consisting of three types of units expressed by the unit formulas of $[R^1R^2SiO_{2/2}]$, $[R^2_2SiO_{2/2}]$ and $[R^2_3SiO_{1/2}]$, in which $R^1$ is preferably a 3,3,3-trifluoropropyl group and $R^2$ is preferably a methyl group, in such a proportion that the molar ratio of $R^1:(R^1+R^2)$ is in the range from 0.05 to 0.5. The powder is useful as an ingredient in a cosmetic or toiletry preparation to effect improved sustainability of the cosmetic finish and decreased unevenness of coloring on human skin.

18 Claims, No Drawings

PARTICLES OF CURED FLUOROSILICONE RUBBER AND COSMETIC PREPARATION CONTAINING SAME

BACKGROUND OF THE INVENTION

The present invention relates to a powder of cured fluorosilicone rubber particles suitable as an additive to a variety of compositions such as paints, synthetic resins, synthetic and natural rubbers, polishing agents, surface-release agents and cosmetic or toiletry preparations. This invention also relates to cosmetic preparations compounded with such a powder.

Fine particles of a cured silicone rubber are known in the prior art as disclosed, for example, in Japanese Patent Publications 3-30620, 4-17986, 4-55611, 6-2820, 6-2821 and 6-11795 and elsewhere. Proposals are made for the application thereof as an additive to a thermosetting epoxy resin, synthetic rubber, pigment, coating composition and others. Furthermore, a proposal is made in Japanese Patents Kokai 7-258026, 7-258027, 8-259419, 8-310915, 8-319215 and 8-319218 for the application of cured silicone rubber particles as an additive to a variety of cosmetic products.

Cosmetic products prepared by compounding conventional cured silicone rubber particles have a serious problem. While it is sometimes the case that a cosmetic preparation is formulated with an oily ingredient such as low molecular weight silicones having cyclic or linear molecular structures including octamethylcyclotetrasiloxane, decamethylcyclopentasiloxane and octamethyltrisiloxane and oily hydrocarbon compounds including liquid paraffin and isoparaffin, namely, these oily ingredients are absorbed by the cured silicone rubber particles resulting in swelling of the particles and consequently leading to a decrease in the opacity of the cosmetic layer on the human skin rendering the complexion of the base skin as see-through more or less. Moreover, the rubber particles in the cosmetic finishing layer on the skin are subject to migration under perspiration or by the movement of the face accompanying the coloring agent in the cosmetic preparation resulting in heavy collapsing of the makeup finish.

It is eagerly desired therefore to develop novel and improved cured silicone rubber particles suitable as additives to cosmetic preparations to be free from the above described problems of conventional cured silicone rubber particles without decreasing the advantages to be obtained by the formulation with fine cured silicone rubber particles.

SUMMARY OF THE INVENTION

In view of the above described problems in the conventional cured silicone rubber particles as an ingredient in cosmetic preparations, the inventors have conducted extensive investigations to obtain fine particles of a cured silicone rubber arriving at an unexpected discovery that the fine cured silicone rubber particles defined below well meet the requirements as an additive to cosmetic preparations.

Thus, the present invention provides fine particles of a cured fluorosilicone rubber consisting of three types of organosiloxane units represented by the unit formulas:

$R^1R^2SiO_{2/2}$; (1)

$R^2{}_2SiO_{2/2}$ (2)

and $R^2{}_3SiO_{1/2}$, (3)

In which $R^1$ is a perfluoroalkyl-substituted alkyl group of the formula $R^f(CH_2)_a-$, $R^f$ being a perfluoroalkyl group having 1 to 20 carbon atoms or, preferably, a trifluoromethyl group and the subscript a being a positive integer not exceeding 6 or, preferably, 2, and $R^2$ is a hydrogen atom or a monovalent hydrocarbon group having 1 to 20 carbon atoms with the proviso that the molar ratio of $R^1$ to $(R^1+R^2)$ is in the range from 0.05 to 0.5.

The cured fluorosilicone rubber particles defined above, preferably, have an average particle diameter in the range from 0.1 to 100 $\mu$m and a rubber hardness of 5 to 90 in the JIS A scale specified in JIS K 6301, when used as an ingredient in cosmetic preparations.

DETAILED DESCRIPTION OF THE PREFERRED EMBODIMENTS

As is described above, the cured fluorosilicone rubber constituting the inventive cured silicone rubber particles is a polyorganosiloxane consisting of three types of the organosiloxane units including two difunctional units expressed by the unit formulas (1) and (2) and a monofunctional units expressed by the unit formula (3) described above.

The difunctional units of the first type are represented by the unit formula $R^1R^2SiO_{2/2}$, in which $R^1$ is a perfluoroalkyl-substituted alkyl group which is preferably a 3,3,3-trifluoropropyl group and $R^2$ is a hydrogen atom or a monovalent hydrocarbon group having 1 to 20 carbon atoms. The perfluoroalkyl group $R^f$ forming a part of the group $R^1$ is exemplified by perfluoromethyl, perfluoroethyl, perfluoropropyl, perfluorobutyl, perfluorohexyl, perfluoroheptyl, perfluorooctyl, perfluorodecyl, perfluorododecyl, perfluorotetradecyl, perfluorohexadecyl, perfluorooctadecyl and perfluoroeicosyl groups, of which perfluoromethyl group is preferred with the subscript a, which is a positive integer of 1 to 6, equal to 2 forming a 3,3,3-trifluoropropyl group as $R^1$. This is because organosilicon compounds having a silicon-bonded 3,3,3-trifluoropropyl group have good availability as compared with organosilicon compounds having other types of perfluoroalkyl-substituted alkyl groups in the molecule in addition to the advantage that the fluorosilicone rubber particles according to this preference can impart good lubricity and smoothness to the cosmetic finish with the cosmetic preparation formulated with the cured silicone rubber particles.

The silicon-bonded group denoted by $R^2$ in each of the three types of the organosiloxane units is a hydrogen atom or a monovalent hydrocarbon group having 1 to 20 carbon atoms exemplified by alkyl groups such as methyl, ethyl, propyl, butyl, pentyl, hexyl, heptyl, octyl, nonyl, decyl, dodecyl, tetradecyl, hexadecyl, octadecyl and eicosyl groups, cycloalkyl groups such as cyclopentyl and cyclohexyl groups, alkenyl groups such as vinyl and allyl groups and aryl groups such as phenyl and tolyl groups. In particular, it is preferable that all or at least 90% by moles of the groups denoted by $R^2$ are methyl groups. When the number of carbon atoms in the group $R^2$, similarly to the perfluoroalkyl group $R^f$ forming the group $R^1$, exceeds 20, a decrease is caused in the lubricity and surface-releasability of the fluorosilicone rubber particles.

It is important that the organopolysiloxane forming the cured fluorosilicone rubber particles contains the groups $R^1$ and $R^2$ in a specified molar proportion determined by the molar ratio of $R^1:(R^1+R^2)$ which should be in the range from 0.05 to 0.5 or, preferably, from 0.1 to 0.4 or, more preferably, from 0.15 to 0.35. When this molar ratio is too small, the fluorosilicone rubber particles do not have fully decreased affinity to oily materials so as to be swollen with the oily ingredient in a cosmetic preparation. When this molar ratio is too large, on the other hand, the rubber particles are deficient in the lubricity and surface-releasability.

When the intended application of the inventive cured fluorosilicone rubber particles is as an additive in a cosmetic preparation, the particles should have an average particle diameter in the range from 0.1 to 100 $\mu$m or, preferably, from 1 to 50 $\mu$m or, more preferably, from 3 to 20 $\mu$m. When the average particle diameter is too small, the particles are deficient in the lubricity and surface-releasability while, when the average particle diameter is too large, the skin surface finished with a cosmetic preparation containing the particles would necessarily feel rough and sandy.

Further it is a desirable condition for the cured fluorosilicone rubber particles as an additive to a cosmetic preparation that the rubber hardness thereof in the JIS A scale is in the range from 5 to 90 or, preferably, from 10 to 80 or, more preferably, from 20 to 70. When the hardness of the particles is too low, the particles are deficient in lubricity and surface-releasability while, when the rubber hardness is too high, the skin surface finished with a cosmetic preparation containing the particles would necessarily feel rough and sandy.

The particle configuration of the inventive cured fluorosilicone rubber particles can be spherical or globular, platelet-formed or irregular without particular limitations for most applications. When intended as an ingredient in cosmetic preparations, the most preferable configuration of the particles is spherical.

The cured fluorosilicone rubber particles can be prepared by utilizing a known crosslinking reaction between organopolysiloxane molecules including the condensation reaction between silicon-bonded methoxy groups and silanolic hydroxyl groups, radical reaction between silicon-bonded mercaptoalkyl groups and silicon-bonded vinyl groups and hydrosilation reaction between silicon-bonded vinyl groups and silicon-bonded hydrogen atoms, of which the last mentioned hydrosilation reaction is the most preferable as the crosslinking reaction in view of the reactivity and efficiency of the process. Namely, the hydrosilation reaction is performed in a mixture of a vinyl group-containing organopolysiloxane and an organohydrogenpolysiloxane in the presence of a platinum catalyst.

The above mentioned vinyl group-containing organopolysiloxane must have at least two vinyl groups bonded to the silicon atoms in a molecule. Although the bonding positions of the vinyl groups in the molecule are not particularly limitative, it is preferable that at least one of the vinyl groups be bonded to the silicon atom at the molecular chain end of the organopolysiloxane. The organic groups other than the vinyl groups can be selected from the fluorine-substituted or unsubstituted monovalent hydrocarbon groups denoted by $R^1$ and $R^2$ defined before.

The molecular structure of the vinyl group-containing organopolysiloxane is not particularly limitative and can be straightly linear, branched or cyclic. Mixtures of organopolysiloxanes having different molecular structures can also be used. Though not particularly limitative, it is desirable that the vinyl group-containing organopolysiloxane has such a molecular weight as to give a viscosity of at least 10 centipoise at 25° C. to the organopolysiloxane in order that the cured fluorosilicone rubber particles may have a rubber hardness of 5 to 90 in the JIS A scale.

The vinyl group-containing organopolysiloxane typically has a straightly linear or cyclic molecular structure represented by the linear structural formula $$Vi_bR^2{}_cSi-O-(-SiR^1R^2-O-)_d-(-SiR^2{}_2-O-)_e-(-SiViR^2-O-)_f-SiR^2{}_cVi_b,$$

In which Vi is a vinyl group, $R^1$ and $R^2$ are each as defined before, the subscripts b and c are each 0, 1, 2 or 3 with the proviso that b+c is 3, the subscript d is a positive integer and the subscripts e and f are each 0 or a positive integer with the proviso that 2b+f is at least 2, or a cyclic structural formula

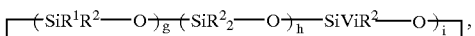

in which the subscript g is a positive integer, the subscript h is 0 or a positive integer and the subscript i is a positive integer of at least 2 with the proviso that g+h+i is in the range from 4 to 10.

The organohydrogenpolysiloxane, which serves as a crosslinking agent for the above described vinyl group-containing organopolysiloxane in the presence of a platinum catalyst for the hydrosilation reaction, must have at least two hydrogen atoms directly bonded to the silicon atoms in a molecule. The organic groups bonded to the silicon atoms can be selected from the fluorine-substituted or unsubstituted monovalent hydrocarbon groups denoted by $R^1$ and $R^2$ defined before.

The molecular structure of the organohydrogenpolysiloxane is not particularly limitative and can be straightly linear, branched or cyclic. Mixtures of organohydrogenpolysiloxanes having different molecular structures can of course be used. Though not particularly limitative, the organohydrogenpolysiloxane should have a molecular weight such that the viscosity thereof at 25° C. does not exceed 10000 centipoise.

The organohydrogenpolysiloxane, which serves as a crosslinking agent for the above described vinyl group-containing organopolysiloxane by the hydrosilation reaction in the presence of a platinum catalyst, can also have a linear or cyclic molecular structure as represented by the linear structural formula $$H_jR^2{}_kSi-O-(-SiR^1R^2-O-)_m-(-SiR^2{}_2-O-)_n-(-SiHR^2-O-)_p-SiR^2{}_kH_j,$$

In which $R^1$ and $R^2$ are each as defined before, the subscripts j and k are each 0, 1, 2 or 3 with the proviso that j+k is 3 and the subscripts m, n and p are each 0 or a positive integer with the proviso that 2j+p is at least 2, or by the cyclic structural formula

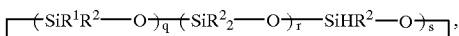

in which the subscript q is a positive integer, the subscript r is 0 or a positive integer and the subscript s is a positive integer of at least 2 with the proviso that q+r+s is in the range from 4 to 10.

The above described organohydrogenpolysiloxane is mixed with the vinyl group-containing organopolysiloxane in such a mixing ratio as to provide from 0.5 to 20 moles or, preferably, from 0.5 to 5 moles of hydrogen atoms directly bonded to the silicon atoms per mole of the vinyl groups in the vinyl group-containing organopolysiloxane. When the amount of the silicon-bonded hydrogen atoms is too small, the crosslinking reaction of the vinyl group-containing organopolysiloxane cannot be fully accomplished while, when the amount of the silicon-bonded hydrogen atoms is too large, a decrease is caused in the mechanical properties of the cured fluorosilicone rubber.

While it is important that the vinyl group-containing organopolysiloxane and the organohydrogenpolysiloxane are mixed uniformly together with a platinum catalyst, it is a further desirable condition that the difference in the molar content of the fluorine-substituted hydrocarbon groups expressed by the ratio of $R^1:(R^1+R^2)$ between the two organosiloxane compounds does not exceed 0.3.

Platinum compounds which serve as a catalyst for promoting the hydrosilation reaction between silicon-bonded vinyl groups and silicon-bonded hydrogen atoms are exemplified by carbon or silica adsorbent carrying platinum, chloroplatinic acid, complexes of chloroplatinic acid with an olefin compound or alcohol, platinum-phosphorus complexes and so on. The amount of the platinum catalyst is in the range from 5 to 100 ppm by weight calculated as platinum based on the total amount of the two organosiloxane compounds. When the amount of the platinum catalyst is too small, full promotion cannot be obtained for the hydrosilation reaction along with an enlarged adverse influence of a catalyst poison while no further improvement can be accomplished in the reaction rate by increasing the amount of the platinum catalyst to exceed the above mentioned upper limit rather with an economical disadvantage due to the expensiveness of the platinum compound.

Several methods are applicable to the preparation of a cured fluorosilicone rubber in the form of fine particles. For example, a crosslinkable liquid composition consisting of the vinyl group-containing organopolysiloxane, organohydrogenpolysiloxane and platinum compound is sprayed into a spray chamber kept at an elevated temperature so that the crosslinking reaction proceeds within the droplets of the liquid composition as atomized to give dried fine particles of a cured fluorosilicone rubber in one step. It is, however, more convenient and advantageous in respect of uniform particle size distribution of the fine cured fluorosilicone rubber particles to conduct the crosslinking reaction in emulsified droplets of a crosslinkable liquid composition comprising the starting organopolysiloxane compounds in an aqueous medium.

Thus, a mixture of a vinyl group-containing organopolysiloxane and organohydrogenpolysiloxane in a specified mixing proportion is added to an aqueous medium containing a surface active agent to be emulsified therein followed by the addition of the platinum catalyst and, if necessary, increasing the temperature.

The surface active agent used as an emulsifying agent should preferably be non-ionic in view of minimizing adverse influences on the crosslinking reaction as compared with surface active agents of other types. Examples of non-ionic surface active agent include polyoxyethylene alkylphenyl ethers, polyoxyethylene alkyl ethers, polyoxyethylene sorbitan fatty acid esters and glycerine fatty acid esters. The amount of the surface active agent added to the aqueous medium is in the range from 0.01 to 20 parts by weight or, preferably, from 0.05 to 10 parts by weight per 100 parts by weight of the emulsion as a whole. When the amount of the surface active agent is too small, the emulsified droplets of the liquid composition cannot be fine enough. When the amount thereof is too large, the fine cured fluorosilicone rubber particles bear an excessively large amount of the surface active agent adsorbed thereon that can only be removed by washing with water with a great difficulty.

The total amount of the vinyl group-containing organopolysiloxane and the organohydrogenpolysiloxane emulsified as a mixture in an aqueous medium is in the range from 1 to 80 parts by weight or, preferably, from 10 to 60 parts by weight per 100 parts by weight of the emulsion as a whole. When the amount of the organosiloxane mixture is too small, the productivity of the process for the preparation of the particles cannot be high enough. When the amount thereof is too large, good emulsification of the siloxane mixture can hardly be obtained.

In an optional case where the cured fluorosilicone rubber particles are desired to contain certain additives such as silicone oils, silane compounds and inorganic and organic filler particles, these additives can be added in advance to the mixture of the starting organosiloxane compounds before emulsification.

The aqueous emulsion of the organopolysiloxane mixture is then admixed with the platinum catalyst and further agitated, if necessary, under heating to effect the hydrosilation reaction within the emulsified liquid droplets so that fine cured fluorosilicone rubber particles can be obtained. It is optional that the reaction rate is controlled adequately by the addition of a known controlling agent for the hydrosilation reaction. When the platinum catalyst and/or the controlling agent are difficult to disperse in the aqueous medium, it is advantageous that the additives are suspended in a small volume of water containing a surface active agent and then the suspension is introduced into the aqueous emulsion of the organopolysiloxane mixture.

After completion of the crosslinking reaction to form fine particles of a cured fluorosilicone rubber, the reaction mixture at room temperature or at an elevated temperature not exceeding 90° C. is admixed with a water-soluble inorganic salt such as sodium sulfate and magnesium sulfate as a salting-out agent and/or a water-miscible alcoholic solvent such as methyl and ethyl alcohols so as to destroy the emulsion. The thus precipitated rubber particles are collected by filtration under pressurization followed, if necessary, by washing with water to remove the salting-out agent and surface active agent and then drying. If the thus dried particles are in the form of an agglomerated cake, it is optional to disintegrate the agglomerated cake into discrete particles using a suitable machine.

As mentioned before, the most promising application of the fine particles of the cured fluorosilicone rubber according to the present invention is as an additive ingredient in various kinds of cosmetic preparations which may contain, besides the inventive cured rubber particles, various kinds of base ingredients acceptable as constituents of cosmetic preparations including other powder materials, binding oils, surface active agents, perfumes, antiseptic agents and solvents according to the respective formulations.

The procedure for the preparation of a cosmetic preparation containing the inventive fine particles of cured fluorosilicone rubber is not particularly limitative and any of conventional known methods are applicable thereto. For example, the particles are first blended with other additive ingredients by using a suitable blending machine such as Henschel mixers, Supermixers, V-blenders, machine mortars-and-pestles and Nauter mixers to give an additive blend which is then blended with a separately prepared mixture of the base ingredients including the binding oils, surface active agents and the like by using a ribbon blender, planetary mixer and the like. The thus obtained blend can be, if necessary, compressed into the form of a compact depending on the intended use of the cosmetic composition.

The amount of the inventive fine particles of cured fluorosilicone rubber in a cosmetic composition is usually in the range from 0.1 to 50 parts or, preferably, from 1 to 40 parts or, more preferably, from 5 to 30 parts by weight per 100 parts by weight of the overall amount of the cosmetic preparation though widely variable depending on the particular type of cosmetic preparations. When the amount of the rubber particles is too small, the desired improvements to be accomplished by the addition of the particles, such as a smooth and non-sticky touch feeling, can hardly be obtained as a matter of course. When the amount thereof is too large, the cosmetic preparation may impart the user with a rough and foreign feeling as well as an eventual non-even coloring by the cosmetic preparation.

A variety of preparation forms can be named for the cosmetic and toiletry preparations compounded with the inventive fine particles of a cured fluorosilicone rubber. They include but are not limited to foundations, creams, powdery preparations, e.g., deodorant powders, pressed powder compacts, face powders and shaving powders, make-up cosmetic preparations, e.g., lipsticks, eye shadows, mascaras and eyeliners, cleansing compositions, e.g., dry shampoos and cosmetic removers, and antiperspirants of the roll-on and spray types.

In the following, the present invention is described in more detail by way of Examples. The viscosity values appearing in the following Examples were all obtained by measurement at 25° C. Procedures for measuring the rubber hardness in the JIS A scale, particle diameter and oil absorption of the fine particles of the cured fluorosilicone rubber are also given. In the following descriptions, the term "parts" appearing relative to the amount of an ingredient in the formulation of cosmetic or toiletry preparations always refers to "parts by weight".

(1) Rubber Hardness

Since no method was available for the determination of the rubber hardness of a single fine rubber particle, measurement of the rubber hardness was undertaken for a bulk sample of the cured rubber prepared under conditions simulating those in the preparation of the rubber particles. Thus, a 50 g portion of a mixture of the same vinyl group-containing organopolysiloxane and organohydrogenpolysiloxane in the same mixing proportion was uniformly admixed with 0.20 g of a toluene solution of a chloroplatinic acid-divinyltetramethyldisiloxane complex in a concentration of 0.5% by weight as platinum and 0.10 g of 2-methyl-2-trimethylsiloxy-3-butene as a controlling agent. A 26 g portion of the thus prepared mixture was placed in an aluminum dish of 60 mm inner diameter and 9.5 mm depth and kept standing for 4 hours at room temperature followed by heating at 60° C. for 12 hours to effect curing of the organopolysiloxane mixture into a mass of a cured rubber. After cooling to 25° C., the rubber hardness was determined according to the procedure specified in JIS K 6301 by using the JIS-A durometer.

(2) Average Particle Diameter and Particle Configuration

Optical microscope photographs were taken of the cured fluorosilicone rubber particles to calculate the average particle diameter and observe the particle configuration.

(3) Oil Absorption

A 5.0 g portion of the cured fluorosilicone rubber particles was placed in a glass bottle of greater than 50 ml capacity and 50 g of decamethylcyclopentasiloxane were added thereto. The bottle was stoppered and thoroughly shaken for 10 minutes on a shaking machine to give a uniform dispersion of the particles in the liquid medium. After standing as such at room temperature for 3 days or 7 days, the dispersion was pressure filtered at 1 kg/cm². The cake of the particles wet with the liquid siloxane was weighed to determine the weight increase over the dry weight and the values were recorded as the oil absorption A3 and A7 for 3 days or 7 days absorption time, respectively, as g per 5.0 g of dry powder.

Separately, the same testing procedure as above was undertaken excepting for the replacement of decamethylcyclopentasiloxane with the same amount of a dimethylpolysiloxane oil having a viscosity of 6 centistokes at 25° C. to give oil absorption values B3 and B7 for the powder dispersion stood for 3 days or 7 days, respectively.

EXAMPLE 1

A mixture was prepared from 446.6 g of a 3,3,3-trifluoropropyl group-containing diorganopolysiloxane, referred to as the siloxane (a1) hereinafter, expressed by the formula

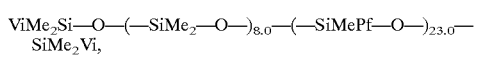

in which Me is a methyl group, Vi is a vinyl group and Pf is a 3,3,3-trifluoropropyl group, and 53.4 g of a 3,3,3-trifluoropropyl group-containing organohydrogenpolysiloxane, referred to as the siloxane (b1) hereinafter, expressed by the formula

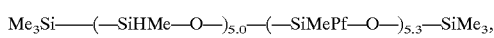

In which Me and Pf each have the same meaning as defined above. This mixture was admixed with a uniform aqueous solution of 4.0 g of a polyoxyethylene lauryl ether having an HLB value of 13.6 (Emulgen 109P, a product by Kao Co.) in 60 g of water and the resultant mixture was agitated with a homomixer rotating at 5000 rpm to give an oil-in-water emulsion having high consistency. After continued agitation for 10 minutes, revolution of the homomixer was dropped to 2000 rpm and the emulsion was admixed with 436 g of water to give 1000 g of a uniformly diluted oil-in-water emulsion.

Next, the emulsion was admixed with a mixture of 4.0 g of a toluene solution of a chloroplatinic acid-divinyltetramethyldisiloxane complex in a concentration of 0.5% by weight calculated as platinum and 8.0 g of the same surface active agent as used above. Continued gentle agitation of the resultant emulsion for 24 hours at room temperature effected crosslinking between the siloxanes (a1) and (b1) by the hydrosilation reaction. Thereafter, the emulsion was destroyed by salting-out by adding sodium sulfate to the emulsion heated at 80° C. The obtained coagulate of cured fluorosilicone rubber particles was washed three times with 1000 ml of water to remove the residual sodium sulfate and surface active agent. Drying in a hot-air circulation oven at 105° C. for 12 hours and disintegration of the dried mass by a mixing machine yielded a white powder, referred to as the silicone rubber powder 1 hereinafter, of fine cured fluorosilicone rubber particles having a spherical particle configuration.

A small portion of the silicone rubber powder 1 was dispersed and suspended in a volume of water containing a surface active agent. The aqueous suspension was subjected to the measurement of the average particle diameter of the cured fluorosilicone rubber particles using a Coulter Counter (trade name, manufactured by Coulter Electronics Co.) to obtain a value of 5 μm.

Table 1 below gives the molar proportion of the 3,3,3-trifluoropropyl groups, Pf, to the total of Pf and methyl groups, Me, i.e. Pf:(Pf+Me), rubber hardness of the cured fluorosilicone rubber and oil absorption of silicone rubber powder 1, i.e. the values of A3 and A7 in decamethylcyclopentasiloxane after 3 days and 7 days, respectively, and B3 and B7 in a dimethylpolysiloxane oil after 3 days and 7 days, respectively, as mentioned before.

EXAMPLE 2

Another powder of cured fluorosilicone rubber particles, referred to as silicone rubber powder 2 hereinafter, was prepared in substantially the same manner as in Example 1 excepting for the replacement of 446.6 g of siloxane (a1) with a combination of 284.9 g of the same siloxane (a1) and 142.4 g of another fluorine-containing diorganopolysiloxane, referred to as siloxane (a2) hereinafter, expressed by the structural formula

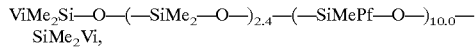
ViMe$_2$Si—O—(—SiMe$_2$—O—)$_{2.4}$—(—SiMePf—O—)$_{10.0}$—SiMe$_2$Vi, in which each symbol has the same meaning as defined before, and an increase of the amount of the siloxane (b1) from 53.4 g to 72.7 g.

The particles of silicone rubber powder 2 had a spherical configuration and an average particle diameter of 5 μm. Table 1 below summarizes the values of Pf:(Pf+Me), rubber hardness and oil absorption.

EXAMPLE 3

A third powder of cured fluorosilicone rubber particles, referred to as silicone rubber powder 3 hereinafter, was prepared in substantially the same manner as in Example 1 excepting for the replacement of 446.6 g of siloxane (a1) with a combination of 209.0 g of siloxane (a1) and 209.9 g of siloxane (a2) and an increase in the amount of siloxane (b1) from 53.4 g to 81.5 g.

The particles of silicone rubber powder 3 had a spherical configuration and an average particle diameter of 5 μm. Table 1 below summarizes the values of Pf:(Pf+Me), rubber hardness and oil absorption.

EXAMPLE 4

A fourth powder of cured fluorosilicone rubber particles, referred to as silicone rubber powder 4 hereinafter, was prepared in substantially the same manner as in Example 1 excepting for the replacement of 446.6 g of siloxane (a1) with 441.6 g of a third fluorine-containing diorganopolysiloxane, referred to as siloxane (a3) hereinafter, expressed by the structural formula ViMe$_2$Si—O—(—SiMe$_2$—O—)$_{14.6}$—(—SiMePf—O—)$_{16.2}$—SiMe$_2$Vi, in which each symbol has the same meaning as defined before, and an increase in the amount of siloxane (b1) from 53.4 g to 58.4 g.

The particles of silicone rubber powder 4 had a spherical configuration and an average particle diameter of 5 μm. Table 1 below summarizes the values of Pf:(Pf+Me), rubber hardness and oil absorption.

EXAMPLE 5

A fifth powder of cured fluorosilicone rubber particles, referred to as silicone rubber powder 5 hereinafter, was prepared in substantially the same manner as in Example 1 excepting for the replacement of 446.6 g of siloxane (a1) with 439.5 g of a fourth fluorine-containing diorganopolysiloxane, referred to as siloxane (a4) hereinafter, expressed by the structural formula

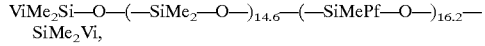
ViMe$_2$Si—O—(—SiMe$_2$—O—)$_{25.3}$—(—SiMePf—O—)$_{12.1}$—SiMe$_2$Vi, in which each symbol has the same meaning as defined before, and an increase in the amount of siloxane (b1) from 53.4 g to 60.5 g.

The particles of silicone rubber powder 5 had a spherical configuration and an average particle diameter of 5 μm. Table 1 below summarizes the values of Pf:(Pf+Me), rubber hardness and oil absorption.

Comparative Example 1

A sixth powder of cured fluorosilicone rubber particles, referred to as silicone rubber powder 6 hereinafter, was prepared in substantially the same manner as in Example 1 excepting for the replacement of 446.6 g of siloxane (a1) with 414.9 g of a fifth fluorine-containing diorganopolysiloxane, referred to as the siloxane (a5) hereinafter, expressed by the structural formula

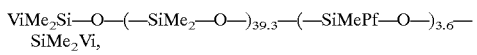
ViMe$_2$Si—O—(—SiMe$_2$—O—)$_{39.3}$—(—SiMePf—O—)$_{3.6}$—SiMe$_2$Vi, in which each symbol has the same meaning as defined before, and replacement of 53.4 g of siloxane (b1) with 85.1 g of another organohydrogenpolysiloxane, referred to as siloxane (b2) hereinafter, expressed by the structural formula

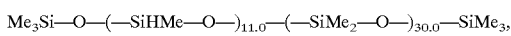
Me$_3$Si—O—(—SiHMe—O—)$_{11.0}$—(—SiMe$_2$—O—)$_{30.0}$—SiMe$_3$, in which Me is a methyl group.

The particles of silicone rubber powder 6 had a spherical configuration and an average particle diameter of 5 μm. Table 1 below summarizes the values of Pf:(Pf+Me), rubber hardness and oil absorption.

Comparative Example 2

A seventh powder of cured silicone rubber particles, referred to as silicone rubber powder 7 hereinafter, was prepared in substantially the same manner as in Comparative Example 1 excepting for the replacement of 414.9 g of siloxane (a5) with 483.0 g of a fluorine-free diorganopolysiloxane, referred to as siloxane (a6) hereinafter, expressed by the structural formula

ViMe$_2$Si—O—(—SiMe$_2$—O—)$_{180}$—SiMe$_2$Vi, in which each symbol has the same meaning as defined before, and a decrease in the amount of the siloxane (b2) from 85.1 g to 17.0 g.

The particles of silicone rubber powder 7 had a spherical configuration and an average particle diameter of 5 μm. Table 1 below summarizes the values of rubber hardness and oil absorption.

TABLE 1

|  |  | Example | | | | | Comparative Example | |
|---|---|---|---|---|---|---|---|---|
|  |  | 1 | 2 | 3 | 4 | 5 | 1 | 2 |
| Pf: (Pf + Me), by moles | | 0.33 | 0.32 | 0.32 | 0.22 | 0.16 | 0.04 | 0 |
| Rubber hardness, JIS-A | | 23 | 30 | 36 | 26 | 26 | 28 | 29 |
| Oil absorption, g/5 g | A3 | 1.8 | 1.7 | 1.7 | 3.2 | 7.1 | 15.6 | 18.3 |
|  | B3 | 2.2 | 1.8 | 1.7 | 2.2 | 3.2 | 9.2 | 12.0 |
|  | A7 | 2.1 | 2.2 | 2.2 | 3.8 | 7.2 | 16.0 | 18.9 |
|  | B7 | 2.0 | 2.0 | 1.9 | 2.5 | 3.3 | 9.5 | 12.0 |

EXAMPLE 6

A cosmetic foundation composition was prepared according to the formulation given below and including one of the cured fluorosilicone rubber powders prepared above. The silicone oil as ingredient (7) was a dimethyl silicone oil having a viscosity of 6 centistokes at 25° C.

| (1) Talc | 61.0 parts |
|---|---|
| (2) Titanium dioxide | 10.0 |
| (3) Silicone rubber powder 1 | 10.0 |
| (4) Stearic acid | 1.5 |
| (5) Glycerin monostearate | 0.5 |
| (6) Myristyl alcohol | 0.5 |
| (7) Silicone oil | 15.0 |
| (8) Triethanolamine | 0.5 |
| (9) Polyethyleneglycol | 1.0 |
| (10) Antiseptic agent | q.s. |
| (11) Perfume | q.s. |

Thus, ingredients (4) through (7) were mixed and heated together at 85° C. to give a uniform mixture. To this were added ingredients (8) through (10) followed by cooling to room temperature. This mixture was added, together with ingredient (11), to a mixture of ingredients (1) through (3) by agitation for 5 minutes in a Henschel mixer and the mixture was further agitated in a ribbon mixer followed by disintegration into a fine powder that was press-compacted in a case to give a product of foundation.

The thus prepared powder-compact foundation was subjected to an organoleptic evaluation test by 10 female expert panel members to evaluate sustainability of the cosmetic finish and unevenness in coloring. Recording was made of the numbers of the panel members who reported their evaluation of acceptability. The results are shown in Table 2 below.

EXAMPLES 7 to 10

The formulation and the procedure for the preparation of a powder-compacted foundation in each of these four Examples were substantially the same as in Example 6 excepting for the replacement of silicone rubber powder 1 with the same amount of silicone rubber powder 2, 3, 4 or 5, respectively.

Table 2 shows the results of the organoleptic evaluation tests of these foundations.

Comparative Examples 3 and 4

The formulation and the procedure for the preparation of a powder-compacted foundation in each of these Comparative Examples were substantially the same as in Example 6 excepting for the replacement of silicone rubber powder 1 with the same amount of silicone rubber powder 6 or 7, respectively.

Table 2 shows the results of the organoleptic evaluation tests of these foundations.

EXAMPLE 11

An eye shadow powder compact was prepared according to the formulation and preparation procedure given below.

| (1) Colored mica titanium | 60.0 parts |
|---|---|
| (2) Silicone rubber powder 1 | 15.0 |
| (3) Zinc laurate | 10.0 |
| (4) Decamethylcyclopentasiloxane | 10.0 |
| (5) Octylpalmitate | 5.0 |
| (6) Antioxidant | q.s. |

-continued

| (7) Antiseptic agent | q.s. |
|---|---|
| (8) Perfume | q.s. |

A mixture was prepared by blending the ingredients (1) through (3) for 5 minutes in a Henschel mixer and then admixed with a uniform mixture of the ingredients (4) through (8). After mixing in a ribbon blender to give a umiform composition, the composition was disintegrated into a fine powder and compressed into a powder compact.

The results of the organoleptic evaluation tests of this eye shadow compact are shown in Table 2.

EXAMPLES 12 to 15

The formulation and the procedure for the preparation of an eye shadow compact in each of these four Examples were substantially the same as in Example 11 excepting for the replacement of silicone rubber powder 1 with the same amount of silicone rubber powder 2, 3, 4 or 5, respectively.

Table 2 shows the results of the organoleptic evaluation tests of these eye shadow compacts.

Comparative Examples 5 and 6

The formulation and the procedure for the preparation of an eye shadow compact in each of these Comparative Examples were substantially the same as in Example 11 excepting for the replacement of silicone rubber powder 1 with the same amount of silicone rubber powder 6 or 7, respectively.

Table 2 shows the results of the organoleptic evaluation tests of these eye shadow compacts.

TABLE 2

| | | Sustainability of cosmetic finish | Unevenness in coloring |
|---|---|---|---|
| Example | 6 | 10 | 10 |
| | 7 | 10 | 10 |
| | 8 | 10 | 10 |
| | 9 | 10 | 9 |
| | 10 | 9 | 8 |
| | 11 | 10 | 10 |
| | 12 | 10 | 10 |
| | 13 | 10 | 10 |
| | 14 | 9 | 10 |
| | 15 | 8 | 9 |
| Comparative Example | 3 | 6 | 7 |
| | 4 | 3 | 4 |
| | 5 | 6 | 7 |
| | 6 | 3 | 4 |

What is claimed is:

1. A cured fluorosilicone rubber in the form of particles having an average diameter in the range from 0.1 to 100 $\mu$m and a rubber hardness in the range from 5 to 90 in the JIS A scale, the fluorosilicone rubber having a composition consisting of the first type units of the unit formula $[R^1R^2SiO_{2/2}]$, second type units of the unit formula $[R^2{}_2SiO_{2/2}]$ and third type units of the unit formula $[R^2{}_3SiO_{1/2}]$, in which $R^1$ is a perfluoroalkyl-substituted alkyl group represented by the general formula $R^f(CH_2)_a$—, $R^f$ being a perfluoroalkyl group having 1 to 20 carbon atoms and the subscript a being a positive integer not exceeding 6, and $R^2$ is a hydrogen atom or a monovalent hydrocarbon group having 1 to 20 carbon atoms, in such a proportion that the molar ratio of $R^1:(R^1+R^2)$ is in the range from 0.05 to 0.5.

2. The cured fluorosilicone rubber in the form of particles as claimed in claim 1 in which the group denoted by $R^1$ is a 3,3,3-trifluoropropyl.

3. The cured fluorosilicone rubber in the form of particles as claimed in claim 1 in which the group denoted by $R^2$ is a methyl group.

4. The cured fluorosilicone rubber in the form of particles as claimed in claim 1 in which the molar ratio of $R^1:(R^1+R^2)$ is in the range from 0.1 to 0.4.

5. The cured fluorosilicone rubber in the form of particles as claimed in claim 4 in which the molar ratio of $R^1:(R^1+R^2)$ is in the range from 0.15 to 0.35.

6. The cured fluorosilicone rubber in the form of particles as claimed in claim 1 in which the average diameter of the particles is in the range from 1 to 50 µm.

7. The cured fluorosilicone rubber in the form of particles as claimed in claim 6 in which the average diameter of the particles is in the range from 3 to 20 µm.

8. The cured fluorosilicone rubber in the form of particles as claimed in claim 1 in which the rubber hardness of the cured fluorosilicone rubber is in the range from 10 to 80 in the JIS A scale.

9. The cured fluorosilicone rubber in the form of particles as claimed in claim 8 in which the rubber hardness of the cured fluorosilicone rubber is in the range from 20 to 70 in the JIS A scale.

10. The cured fluorosilicone rubber in the form of particles as claimed in claim 1 in which the particles each have a spherical configuration.

11. A cosmetic preparation which comprises:
    (A) a cured fluorosilicone rubber in the form of particles having an average diameter in the range from 0.1 to 100 µm and a rubber hardness in the range from 5 to 90 in the JIS A scale, the fluorosilicone rubber having a composition consisting of the first type units of the unit formula $[R^1R^2SiO_{2/2}]$, second type units of the unit formula $[R^2{}_2SiO_{2/2}]$ and third type units of the unit formula $[R^2{}_3SiO_{1/2}]$, in which $R^1$ is a perfluoroalkyl-substituted alkyl group represented by the general formula $R^f(CH_2)_a-$, $R^f$ being a perfluoroalkyl group having 1 to 20 carbon atoms and the subscript a being a positive integer not exceeding 6, and $R^2$ is a hydrogen atom or a monovalent hydrocarbon group having 1 to 20 carbon atoms, in such a proportion that the molar ratio of $R^1:(R^1+R^2)$ is in the range from 0.05 to 0.5; and
    (B) ingredients acceptable as the base ingredients of a cosmetic preparation.

12. The cosmetic preparation as claimed in claim 11 in which the amount of the component (A) is in the range from 0.1 to 50 parts by weight per 100 parts by weight of the total amount of the component (A) and component (B).

13. The cosmetic preparation as claimed in claim 12 in which the amount of the component (A) is in the range from 1 to 40 parts by weight per 100 parts by weight of the total amount of the component (A) and component (B).

14. The cosmetic preparation as claimed in claim 13 in which the amount of the component (A) is in the range from 5 to 30 parts by weight per 100 parts by weight of the total amount of the component (A) and component (B).

15. The cured fluorosilicone rubber in the form of particles as claimed in claim 1 wherein $R^2$ is, in each case independently, a methyl, ethyl, propyl, butyl, pentyl, hexyl, heptyl, octyl, nonyl, decyl, dodecyl, tetradecyl, hexadecyl, octadecyl, eicosyl, cyclopentyl, cyclohexyl, vinyl, allyl, phenyl or tolyl group.

16. The cured fluorosilicone rubber in the form of particles as claimed in claim 1 wherein a is 2.

17. The cured fluorosilicone rubber in the form of particles as claimed in claim 1 wherein $R^f$ is a perfluoromethyl, perfluoroethyl, perfluoropropyl, perfluorobutyl, perfluorohexyl, perfluoroheptyl, perfluorooctyl, perfluorodecyl, perfluorododecyl, perfluortetradecyl, perfluorohexadecyl, perfluorooctadecyl and perfluoroeicosyl group.

18. The cured fluorosilicone rubber in the form of particles as claimed in claim 1 wherein the cured fluorosilicone rubber particles are a dry powder.

* * * * *